(12) United States Patent
Skarda et al.

(10) Patent No.: US 11,877,783 B2
(45) Date of Patent: Jan. 23, 2024

(54) CARDIAC SURGICAL INSTRUMENT AND CONNECTOR WITH BUILT-IN ELECTROGRAM (EGM) FILTERING CIRCUITRY

(71) Applicant: Medtronic, Inc., Minneapolis, MN (US)

(72) Inventors: James Skarda, Baytown, MN (US); Eric Meyer, Andover, MN (US); Donald W. Heckel, Thornton, MN (US); Travis Jones, Erie, CO (US)

(73) Assignee: Medtronic, Inc., Minneapolis, MN (US)

( * ) Notice: Subject to any disclaimer, the term of this patent is extended or adjusted under 35 U.S.C. 154(b) by 524 days.

(21) Appl. No.: 16/259,691

(22) Filed: Jan. 28, 2019

(65) Prior Publication Data

US 2019/0231413 A1  Aug. 1, 2019

Related U.S. Application Data

(60) Provisional application No. 62/623,455, filed on Jan. 29, 2018.

(51) Int. Cl.
*A61B 18/14* (2006.01)
*A61B 18/08* (2006.01)
(Continued)

(52) U.S. Cl.
CPC ............ *A61B 18/082* (2013.01); *A61B 5/287* (2021.01); *A61B 18/1206* (2013.01);
(Continued)

(58) Field of Classification Search
CPC .............. A61B 18/082; A61B 18/1482; A61B 18/1206; A61B 18/1492; A61B 5/287;
(Continued)

(56) References Cited

U.S. PATENT DOCUMENTS 6,115,628 A  9/2000  Stadler et al.
8,623,010 B2  1/2014  Ocel et al.
(Continued)

FOREIGN PATENT DOCUMENTS

WO   WO 2016/081611 A1   5/2016

OTHER PUBLICATIONS

PCT International Search Report and Written Opinions dated Mar. 22, 2019.
(Continued)

*Primary Examiner* — Michael F Peffley
(74) *Attorney, Agent, or Firm* — Michael Best & Friedrich LLP (57) ABSTRACT

Aspects of the disclosure relate to an instrument for pacing, mapping, sensing, and/or ablating cardiac tissue that includes an electrogram filtering circuit. To supply radio frequency energy, the disclosed instruments are only optionally connected to a radio frequency generator. When connected to a generator, the electrogram filtering circuit can be provided in a handle of the instrument, or in a connector, for example, to protect the instrument from potentially high-powered radio frequency energy. Alternatively, various disclosed embodiments are capable of pacing/sensing as a standalone device. The connector can be provided separately from both the instrument and the generator. In some embodiments, the electrogram filtering circuit is adaptive to suit a variety of generators.

18 Claims, 6 Drawing Sheets

(51) Int. Cl.
*A61B 5/287* (2021.01)
*A61B 18/12* (2006.01)
*A61B 17/00* (2006.01)
*A61B 18/00* (2006.01)
*A61N 1/36* (2006.01)
*A61N 1/362* (2006.01)
*A61B 90/00* (2016.01)
*A61N 1/37* (2006.01)
*A61B 5/00* (2006.01)
*A61N 1/05* (2006.01)
*A61B 5/361* (2021.01)

(52) U.S. Cl.
CPC ...... *A61B 18/1482* (2013.01); *A61B 18/1492* (2013.01); *A61B 5/361* (2021.01); *A61B 5/4836* (2013.01); *A61B 2017/00044* (2013.01); *A61B 2017/00053* (2013.01); *A61B 2018/00178* (2013.01); *A61B 2018/00357* (2013.01); *A61B 2018/00363* (2013.01); *A61B 2018/00404* (2013.01); *A61B 2018/00577* (2013.01); *A61B 2018/00702* (2013.01); *A61B 2018/00791* (2013.01); *A61B 2018/00839* (2013.01); *A61B 2018/00988* (2013.01); *A61B 2090/0807* (2016.02); *A61B 2505/05* (2013.01); *A61N 1/0587* (2013.01); *A61N 1/36017* (2013.01); *A61N 1/3625* (2013.01); *A61N 1/3702* (2013.01)

(58) Field of Classification Search
CPC ......... A61B 5/283; A61B 5/296; A61B 5/313; A61B 5/389
See application file for complete search history.

(56) References Cited

U.S. PATENT DOCUMENTS

| 10,166,062 | B2* | 1/2019 | Panescu | A61B 18/1492 |
| 2002/0007198 | A1* | 1/2002 | Haupert | A61N 1/37235 607/30 |
| 2009/0082691 | A1* | 3/2009 | Denison | A61B 5/30 600/544 |
| 2009/0204171 | A1* | 8/2009 | Ameri | A61N 1/056 607/36 |
| 2012/0116209 | A1* | 5/2012 | Klee | G01R 33/34007 438/381 |
| 2012/0253340 | A1* | 10/2012 | Stevenson | A61N 1/05 606/33 |
| 2013/0006228 | A1 | 1/2013 | Johnson et al. | |
| 2015/0272654 | A1 | 10/2015 | Esch et al. | |
| 2017/0238991 | A1 | 8/2017 | Barry et al. | |

OTHER PUBLICATIONS

NLAS4599/D Low Voltage Single Supply SPDT Analog Switch, Semiconductor Components Industries, LLC, Mar. 2011 (p. 1-11).

* cited by examiner

CARDIAC SURGICAL INSTRUMENT AND CONNECTOR WITH BUILT-IN ELECTROGRAM (EGM) FILTERING CIRCUITRY

CROSS-REFERENCE TO RELATED APPLICATIONS

This Non-Provisional Patent Application claims the benefit of the filing date of U.S. Provisional Patent Application Ser. No. 62/623,455, filed Jan. 29, 2018, the entire teachings of which are incorporated herein by reference.

BACKGROUND

Various devices, such as the Cardioblate® MAPS electrosurgical instrument available from Medtronic, Inc. of Minneapolis, Minnesota integrate cardiac rhythm diagnostic and surgical ablation technologies into one simple-to use device.

Ablation of the abnormal tissue or accessory pathway responsible for atrial fibrillation has proven highly viable. Ablation of tissue is generally achieved by applying the destructive energy source to the target tissue. A highly viable ablation device is the hand-held Cardioblate® MAPS electrosurgical instrument. The instrument rigidly couples the electrode tip to the instrument's handle that is otherwise held and manipulated by the surgeon. The rigid construction of the electrosurgical instrument requires direct, open access to the targeted tissue. Thus, for treatment of atrial fibrillation via an electrosurgical instrument, it is desirable to gain access to the patient's heart through one or more openings in the patient's chest (such as a sternotomy, a thoracotomy, a small incision and/or a port). In addition, the patient's heart may be opened through one or more incisions, thereby allowing access to the endocardial surface of the heart.

Once the target site (e.g., right atrium, left atrium, epicardial surface, endocardial surface, pulmonary veins, etc.) is accessible, the surgeon positions the electrode tip of the electrosurgical instrument at the target site. The tip is then energized, ablating (or for some applications, cauterizing) the contacted tissue. A desired lesion pattern is then created (e.g., portions of a known "Maze" procedure) by moving the tip in a desired fashion along the target site. In this regard, the surgeon can easily control positioning and movement of the tip, as the electrosurgical instrument is rigidly constructed and relatively short (in contrast to a catheter-based ablation technique).

In cases of atrial fibrillation, it is typically desirable to identify the origination point of the undesired electrical impulses prior to ablation. Mapping may be accomplished by placing one or more mapping electrodes into contact with the tissue in question. Mapping of tissue may occur by placing one or more mapping electrodes into contact with the pulmonary veins, endocardial surface of the heart and/or the epicardial surface of the heart.

As used herein, the term "mapping instrument" includes a hand-held instrument capable of pacing and/or mapping cardiac tissue. If not provided as part of the electrosurgical instrument, the mapping instrument can rigidly couple an electrode tip to the instrument's handle that is otherwise held and manipulated by the surgeon. The rigid construction of the mapping instrument requires direct, open access to the targeted tissue. Thus, for mapping and/or pacing of cardiac tissue via the mapping instrument, it is desirable to gain access to the patient's heart through one or more openings in the patient's chest (such as a sternotomy, a thoracotomy, a small incision and/or a port). In addition, the patient's heart may be opened through one or more incisions, thereby allowing access to the endocardial surface of the heart.

Once the target site (e.g., right atrium, left atrium, right ventricle, left ventricle, epicardial surface, endocardial surface, pulmonary veins, etc.) is accessible, the surgeon positions the electrode tip of the mapping instrument at the target site. The surgeon can easily control positioning and movement of the tip, as the mapping instrument is rigidly constructed and relatively short in contrast to a catheter-based technique.

The Cardioblate® MAPS device integrates cardiac rhythm mapping, pacing and sensing as well as surgical ablation. When connected to an RF generator that includes an electrogram (EGM) filtering circuit that is then connected to a programmer/analyzer, the MAPS device can be used to map, ablate, pace and sense cardiac tissue. For example, the MAPS device can be used to apply high frequency stimulation (HFS) to cardiac tissue, such as around the pulmonary vein/atrial junction, to identify sites that may contribute to various cardiac arrhythmias. The device can then be used to ablate and destroy those sites identified through HFS. Ablation of these sites eliminates a potential source of various cardiac arrhythmias. Following ablation, the device can be used to assess the ability of the ablated tissue to contribute to cardiac arrhythmias. For example, the device can be used to establish atrial capture via pacing with the device from an area to be isolated via the formation of the ablation lesion. Once the isolation lesion has been created, the device is used to again pace from the same location as before to attempt atrial capture. Successful conduction block is then proven if atrial capture is not obtained (no corresponding atrial rate change as established prior to ablation). The device can be used to assess the ability of the ablated tissue to contribute to any cardiac arrhythmias via monitoring atrial EGM pre- and post-ablation to confirm entrance block. For example, the device can be used to monitor atrial EGM in the area to be isolated via the formation of an ablation lesion. Once the isolation lesion has been created, the device can monitor atrial EGM on both sides of the lesion for comparison to each other and those measured previously. Successful conduction block is then proven by the absence or reduction of electrical activity in the area isolated by the ablation lesion when compared to atrial activity outside that area. The MAPS device is limited in its abilities in that it only works if it is connected to a generator that includes an EGM filtering circuit, thereby limiting its ability to work with other types of generators. In addition, the MAPS device needs to be connected to a generator that includes an EGM filtering circuit even if the device is only to be used for mapping, pacing, and/or sensing. Therefore, there is a need for a MAPS device that will operate with various generators, including generators that do not include an EGM filtering circuit. Further, there is a need for a MAPS device that will operate as a standalone device for sensing or as a pacing, sensing, and/or mapping device when connected directly to a programmer/analyzer device and/or a pacing device.

The present disclosure addresses problems and limitations associated with the related art.

SUMMARY

Aspects of the present disclosure relate to systems for cardiac rhythm diagnostic and surgical ablation procedures including a generator, instrument, programmer/analyzer and temporary pacer, for example. The system can be suitable for pacing, mapping, sensing, and/or ablating cardiac tissue.

The system further includes an EGM filtering circuit provided exterior to the generator. For example, the EGM filtering circuit can be provided in the instrument or other connector linking the instrument to the generator. When connected to a generator, the EGM filtering circuit protects equipment external to the generator from potentially high-powered radio frequency (RF) energy. Alternatively, various disclosed systems are capable of sensing as a standalone device. The EGM filtering circuit allows the instrument to be connected directly to a pacemaker device or to a programmer/analyzer without being connected to the generator for sending pacing spikes and/or sensing/analyzing EGM signals.

One example instrument includes a handle, an elongated shaft coupled to the handle, an electrically conductive tip at a distal end of the elongated shaft, and a connector for connecting the instrument to a generator and/or a programmer/analyzer and/or a temporary pacer. The connector includes a radio frequency circuit for applying RF energy from a generator. Further, the instrument includes an EGM filtering circuit having a first active line including a first tuned resonant filter; and a second return line including a second tuned resonant filter. In some embodiments, the connector is provided as a standalone device with respect to the generator and the instrument. In this way, the connector can be used with a variety of instruments and is separately replaceable. In further disclosed embodiments, the EGM filtering circuit is adaptive to be compatible with a variety of generators, programmer/analyzers and/or temporary pacers.

DETAILED DESCRIPTION

Specific embodiments of the present disclosure are now described with reference to the figures, wherein like reference numbers indicate identical or functionally similar elements.

Figure 1:
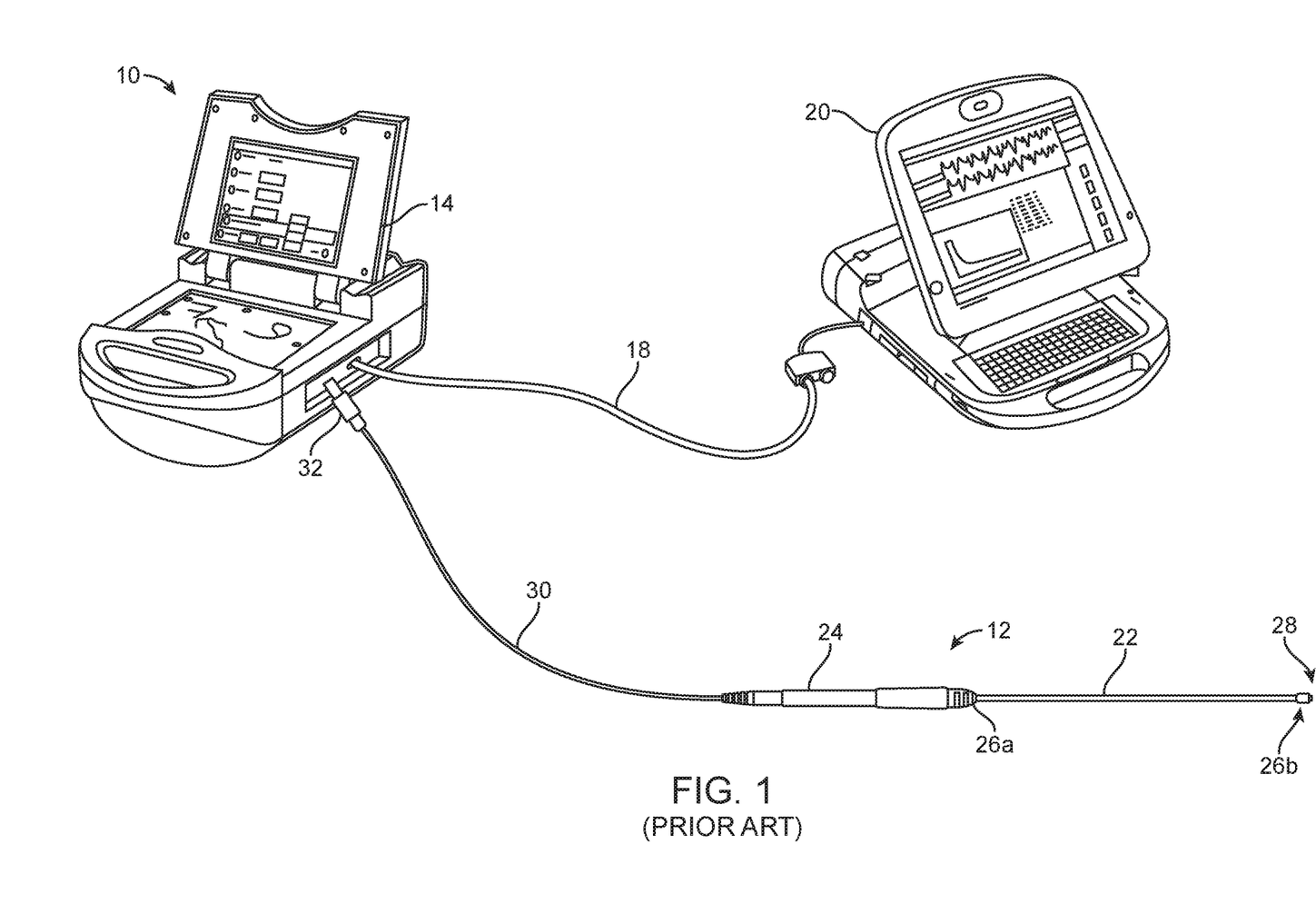
FIG. 1 is a schematic illustration of a known system including a cardiac instrument that can be plugged into a generator with a connector; the system having pacing, mapping, ablation and/or sensing abilities.

Aspects of the disclosure can useful with a wide variety of instruments and systems, including cardiac electrosurgical instruments including pacing, mapping, ablation and/or sensing abilities. An example of one such system 10 is schematically shown in FIG. 1. The system 10 includes an instrument 12 powered by a radio frequency (RF) generator 14 having an electrogram (EGM) filter circuitry (not visible) that is configured to protect any external equipment (e.g., instrument 12 or a programmer/analyzer 20) from the RF energy.

The instrument 12 can be of the type that functions as mapping, ablation, pacing and sensing instrument such as the Cardioblate® MAPS Device available from Medtronic, Inc. or that which is disclosed in U.S. Pat. No. 8,623,010 (Ocel et al.), the disclosure of which is herein incorporated in its entirety by reference. In some embodiments, the instrument 12 is of the type configured to stimulate tissue via the application of high frequency stimulation to areas around a patent's pulmonary vein/arrival junction to identify sites that may contribute to various cardiac arrhythmias. Also, the instrument 12 can be of the type configured to ablate/destroy those sites identified through high frequency stimulate to eliminate a potential source of various cardiac arrhythmias. Additionally, the instrument 12 is of the type configured to establish arterial capture by pacing from the area to be isolated. Once the isolation lesion has been created, the instrument 12 is paced from the same location to attempt atrial capture. A conduction block is proven if atrial capture is not obtained (if not corresponding atrial rate change as established initially). The instrument 12 can also be used to monitor atrial electrogram (EGM) pre- and post-ablation to confirm entrance block. The instrument 12 includes an elongated shaft 22 and a non-conductive handle 24. The shaft 22 defines a proximal section 26a, a distal section 26b, and an internal lumen (not visible) extending from the proximal section 26a. The distal section 26b forms an electrically conductive rounded tip 28 and defines at least one passage (not visible) fluidly connected to the lumen. Attached to the handle 24, via a cable 30, is a connector 32 that can be plugged into a corresponding receptacle (not visible) of the generator 14.

The system 10 further includes an electrogram (EGM) cable 18 interconnecting the programmer/analyzer 20 to the generator 14. The EGM cable 18 is model number 68005 cable available from Medtronic, Inc. of Minneapolis, Minnesota and the programmer/analyzer 20 is the 2090/2290 programmer/analyzer also available from Medtronic, Inc. in this example.

Figure 2:
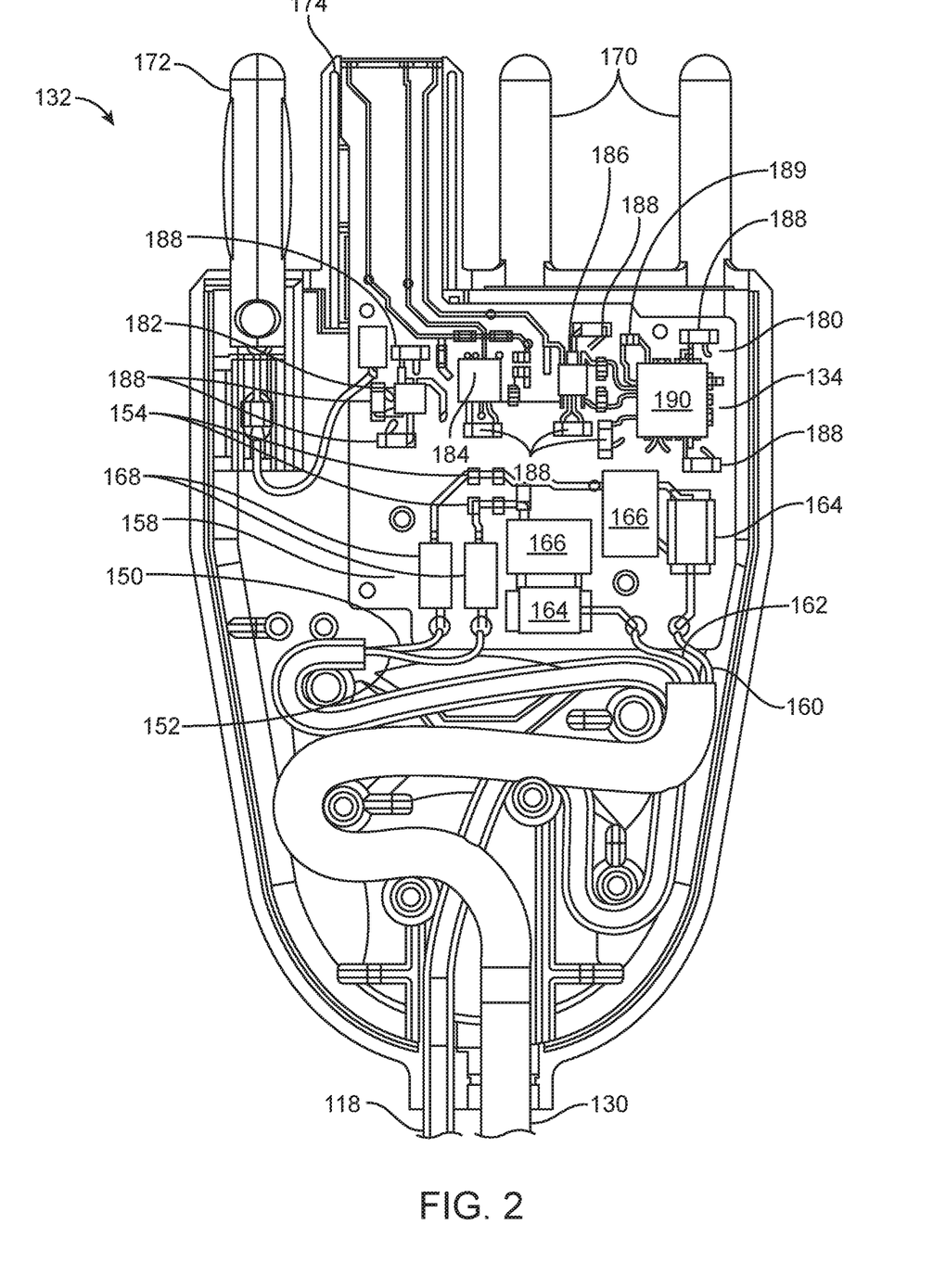
FIG. 2 is a cross-sectional schematic illustration of a connector having EGM filter circuitry.
Figure 3:
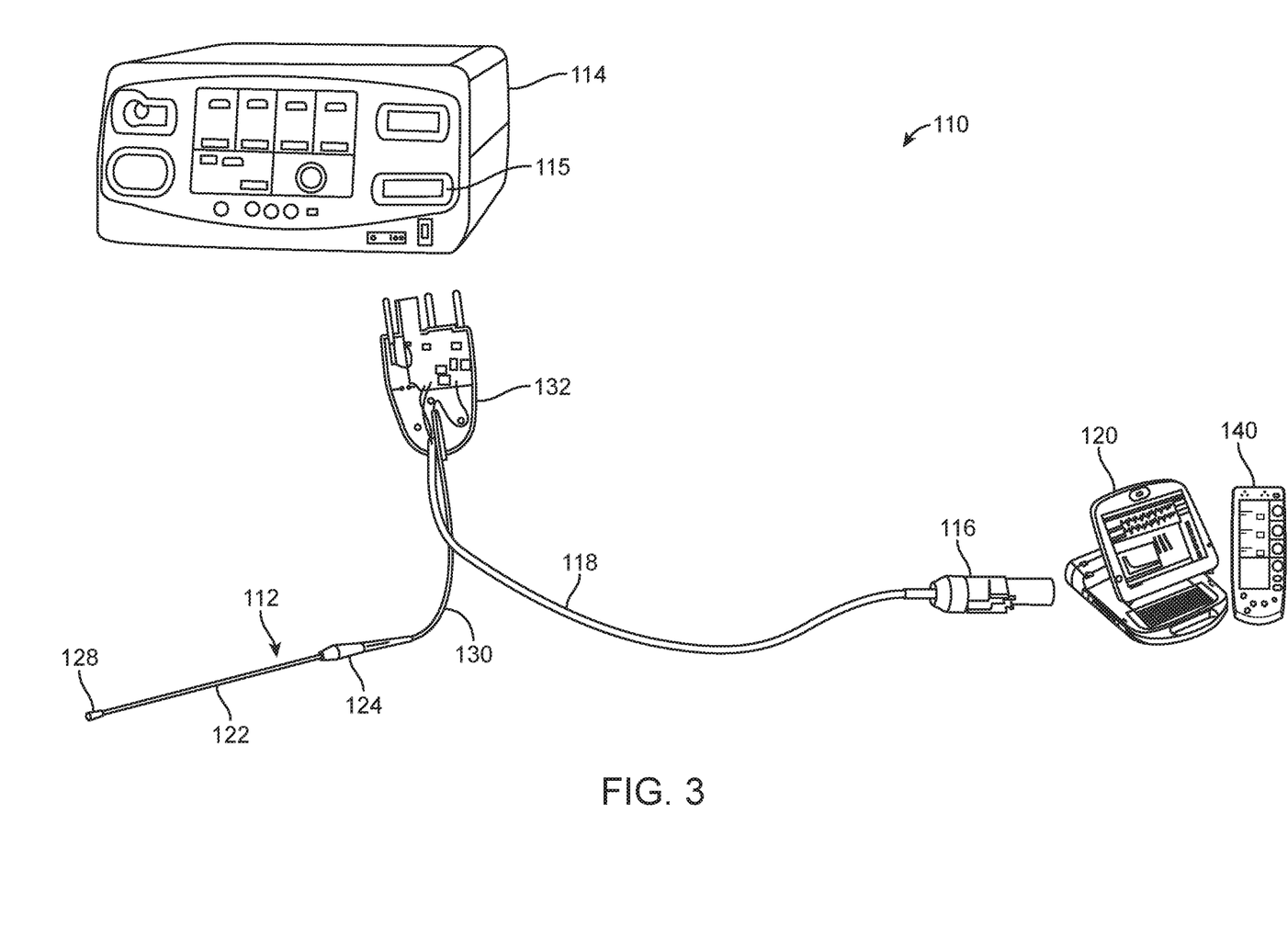
FIG. 3 is a schematic illustration of a system including the connector of FIG. 2.

The schematically depicted system 10 and connector 32 of FIG. 1 can be modified as is schematically illustrated in FIGS. 2-3. System 110 includes an instrument 112 that can be any of the type that, in at least one available mode, would benefit from EGM filtering. One example instrument is an instrument, which is largely similar to that disclosed in Ocel et al. (cited above). The instrument 112 includes a connector 132, which optionally interconnects both the instrument 112 and a programmer/analyzer 120 to a receptacle 115 of a generator 114. One example of a suitable generator 114 is the VLFT10GEN "FT-10" Orion Generator available from Medtronic, Inc. As illustrated, the system 110 can optionally further include a programmer/analyzer 120 such as the 2909/2290 programmer/analyzer or Sirius programmer/analyzer both available from Medtronic, Inc. Alternatively, the connector 132 can be connected to a pacer 140 such as the 5388 or 5392 Temporary Pacers from Medtronic, Inc. It is envisioned that other generators, programmer/analyzers and temporary pacers can be utilized with the disclosed systems of the present disclosure. It is further noted that in FIG. 3, the size of various components are enlarged for ease of illustration and that FIG. 3 is not intended to reflect any particular proportion or size of the illustrated elements.

The connector 132 optionally includes one or more alignment pins 170 that can serve as guides if a power supply pin 172 of the connector 132 is to be connected to the generator 114, via receptacle 115, to supply power to RF circuit 180. Also provided is a generator plug 174 that routes RF energy to an electrically conductive tip 128 of the instrument 112 for ablation procedures. It will be understood that when the instrument 112 is being used for mapping/pacing/sensing, the instrument 112 does not need to be plugged into or powered by the generator 114. In one example embodiment, the RF circuit 180 is positioned on a substrate or board 134 and includes a linear regulator 182 (IC REG LDO 3.3V 0.2 A 6SON such as model number TPS79933DRVR from Texas Instruments Inc. of Dallas, Texas), comparator 184 (IC COMP OTT R-R 44V TSOT-23-5 such as model number LT1716CS5 #TRMPBF from Linear Technology Corp. of Milpitas, California), single power supply buffer gate 186 (IC BUFFER GATE SGL CMOS SC70-5 such as model number SN74LV1T125DCKR from Texas Instruments Inc. of Dallas, Texas), capacitors 188 (CAP 0.10 UF 10V CERAMIC X7R 0603 model number C0603C104K8RACTU from KEMET Electronics Corp. of Simpsonville, South Carolina), resistors 189 (only one representative resistor is labeled, however, a plurality are illustrated) and a field programmable gate array 190 (IC FPGA LCMX02-1200HC 32PIN QFP W/EP such as model number LCMXO2-1200HC-4SG available from Lattice Semiconductor Corp. of Portland, Oregon). The RF circuit 180 and related connector 132 components disclosed in the present application and depicted in FIG. 2 is provided as one example of suitable circuitry for supplying ablative RF energy to an electrode tip of an instrument and the disclosure is not intended to be limited to this specific configuration.

In this example embodiment, the connector 132 includes an instrument cable 130 having respective active and return leads 160, 162 connected to the tip and ring electrodes 128 of the surgical instrument 112 (only a tip electrode is shown in FIG. 3). In addition, the connector 132 further includes or can otherwise be connected to an adapter 116 connected to programmer/analyzer/pacing cable 118 having respective active and return leads 150, 152. The adapter 116 can be plugged into a programmer/analyzer 20 or a pacer 140 that can be separately provided or provided as part of the system 110. The connector 132 further includes electrogram (EGM) filter circuitry 158 (generally referenced) also positioned on the same board 134 as the RF circuitry 180. In other words, the EGM filter circuitry 158 is provided in the same component as and proximate to the RF circuitry 180. The EGM filter circuitry 158 provides a single stage filter that is tuned to the specific frequency of the RF generator 114 to which the instrument 112 is to be connected (e.g., for the VLFT10GEN ("FT-10") generator ~66 dB attenuation @ 434 kHz) and the EGM filter circuitry 158 is configured to protect any equipment external to the generator 114 from the RF energy provided by the generator 114. In one example embodiment, the EGM filter circuitry 158 includes two identical parallel tuned resonant filters, which are connected to respective active/return leads 160, 162 interconnected to the electrodes 128 of the instrument 112 to complete a pacing/sensing circuit. Each tuned resonant filter includes a resistor 154 (RES 20.0 OHM 0603 1% 1/10W such as model number RC0603FR-0720RL available from Yageo Corp. of San Jose, California), an inductor 164 (Fixed Inductors 1812FS High L Filter 1000 uH 5% 19.5 Ohms such as model number 1812F5-105JLC available from Coilcraft Inc. of Cary, Illinois) and a capacitor 166 (CAP CER 150 PF 2 KV 5% NP0 1812 such as model number 1812GA151JAT1A available from AVX Corp. of Fountain Inn, South Carolina). In addition, EMC/EMI signal filtering inductor ferrite chip signal 168 (2000 OHM 1206 SMD) are provided. Signal in and signal return leads 150, 152 complete a programmer/ analyzer circuit (the programmer/analyzer 20 is shown in FIG. 3).

In an alternate embodiment, the EGM filter circuitry 158 can be provided, either with or without the RF circuitry 180, elsewhere in the instrument 112. For example, in one embodiment (not shown), the EGM filter circuitry 158 is provided in a handle 124 of the instrument 112. In such an embodiment, the EGM filter circuitry 158 can be positioned on a flexible board or substrate 134 that is rolled so that that a diameter of the handle 124 can be minimized, while still accommodating the EGM filter circuitry 158 on other circuitry (e.g., the RF circuit 180). The substrate or board 134 can be made of BoPET (biaxially-oriented polyethylene terephthalate) or the like to provide such flexibility.

Figure 4:
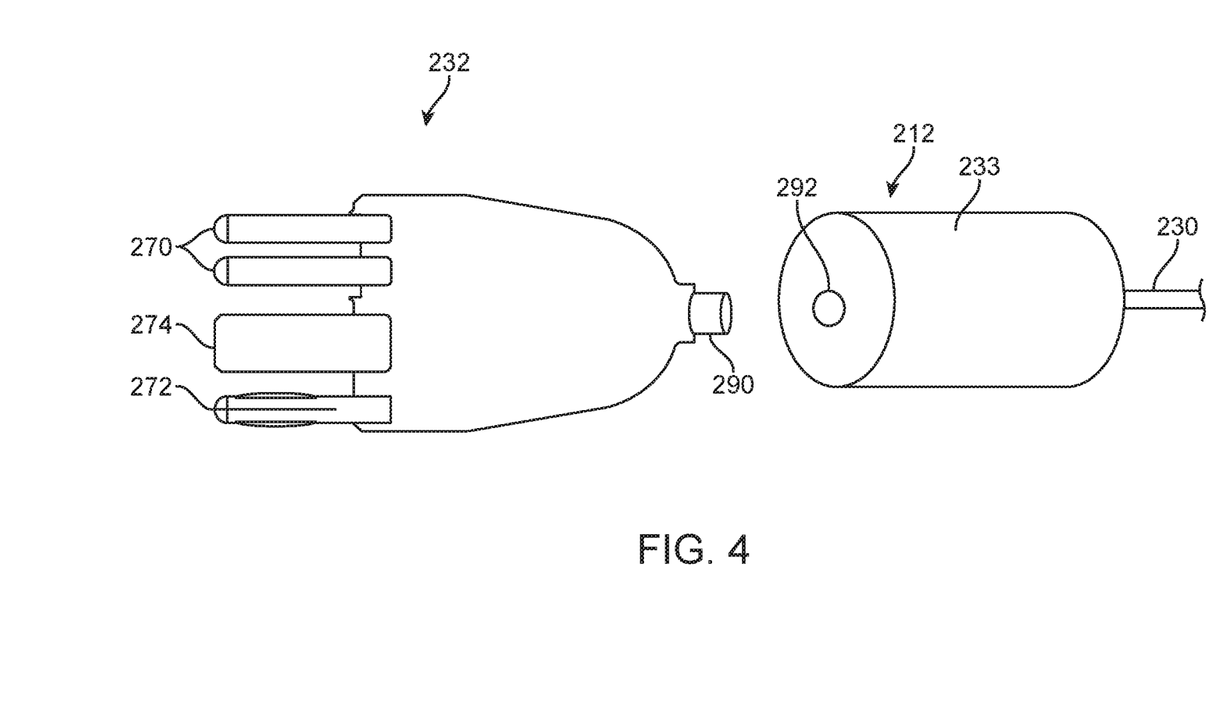
FIG. 4 is a schematic illustration of an alternate stand-alone connector that can be used to connect a cardiac instrument to a generator.

FIG. 4 schematically illustrates yet another embodiment in which a connector 232 is provided as a standalone device separate and removable from an instrument and generator, as described above. In this embodiment, the connector 232 and a corresponding electrosurgical instrument 212 include corresponding adapters 290/292 to releasably secure the connector 232 to the electrosurgical instrument 212. For example, a cable 230 of the electrosurgical instrument 212 can include a hub 233 having an aperture 292 in which a prong 290 of the standalone connector 232 can be inserted for operatively connecting the connector 232 to the instrument 212. With such embodiments, pins 270-274 (similar to pins 170-174) can be covered with a removable cap (not shown) to prevent damage if the system is used for pacing/ sensing functions without a generator attached. This standalone connector 232 can be interchangeably used with a variety of instruments similar in function to instruments 12/112. The connector 232 and instrument 212 of this embodiment can be similar to that those previously disclosed in all other respects. In one embodiment, connector 232 can be configured to be releasably secured to connector 32 of electrosurgical instrument 112. In one embodiment, connector 232 can include cable 118 and connector 116 for connecting the connector 232 to a programmer/analyzer 120 or pacer 140.

Figure 5:
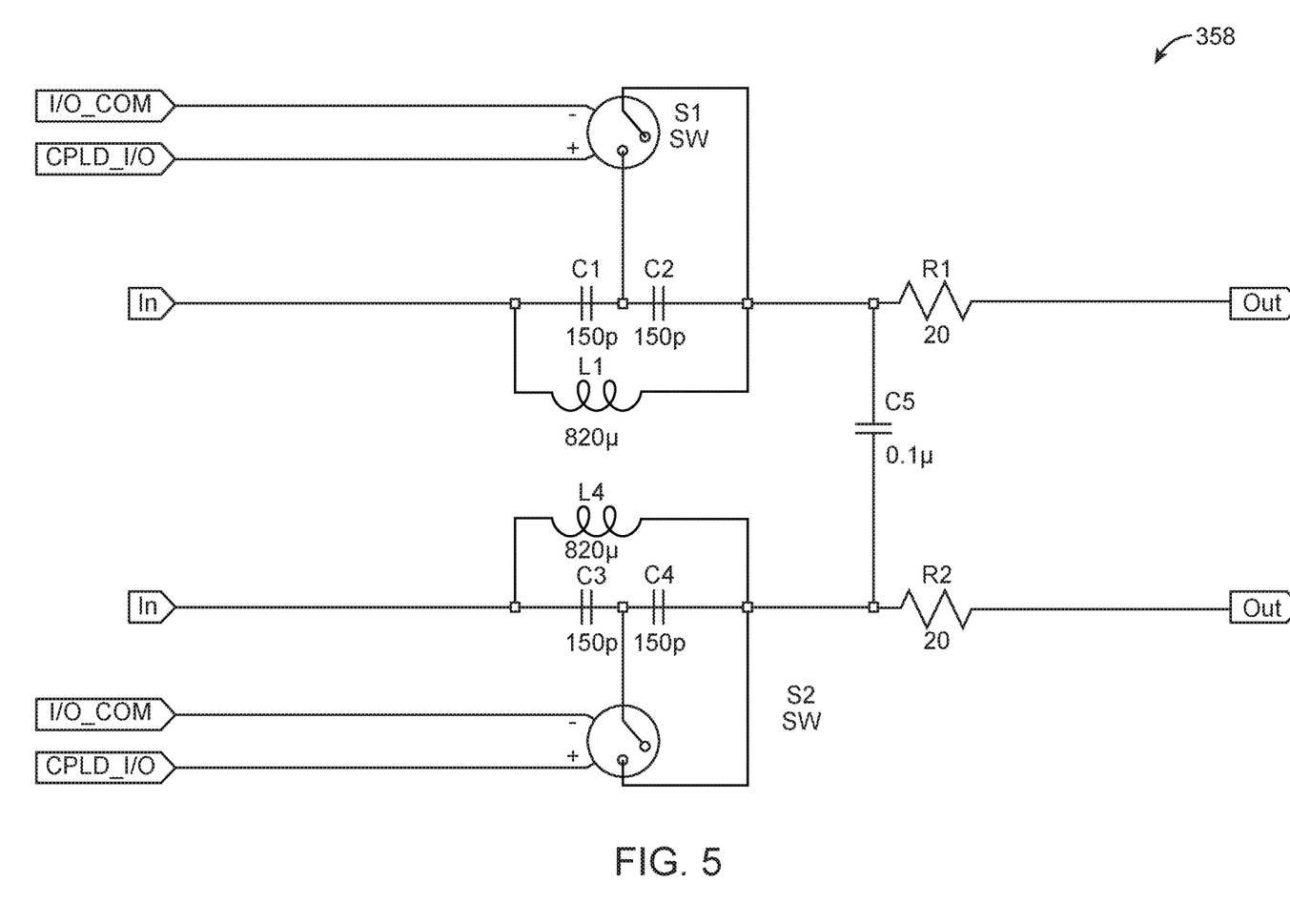
FIG. 5 is a circuit diagram of alternate EGM filter circuitry that is adaptable to suit multiple types of generators.
Figure 6:
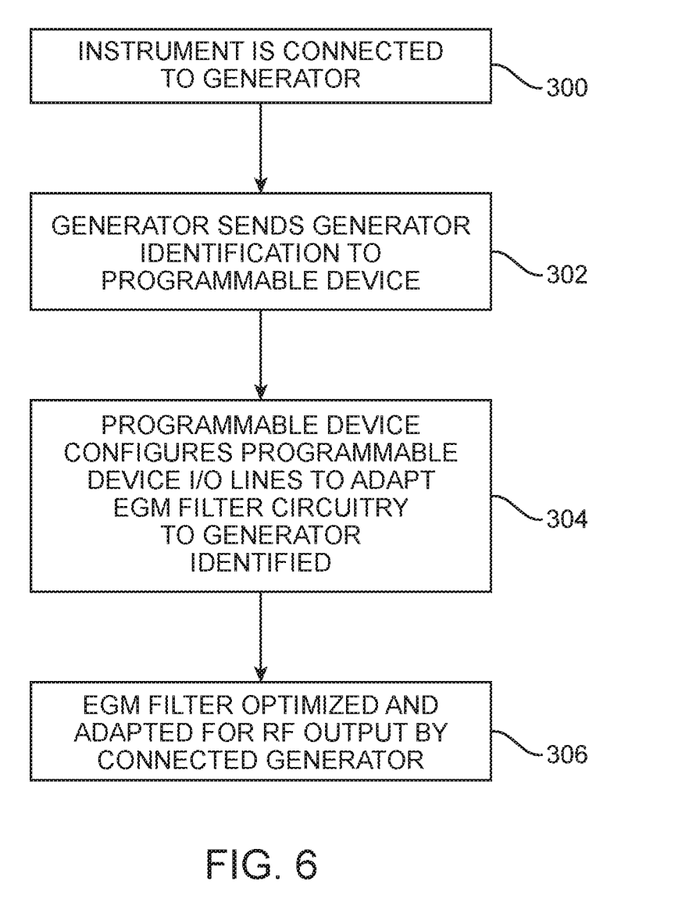
FIG. 6 is a flow chart indicating the process for how the EGM filter circuitry of FIG. 5 adapts to a signal received from a generator.

Yet another embodiment, largely similar to those disclosed above except as otherwise stated, is adaptable to suit a variety of different generators. Many current generators, such as the VLFT10GEN and VLFFX8GEN generators available from Medtronic, Inc. support serial communications through the "smart" monopolar receptacle. The connectors 132 or 232 described above can be modified to include EGM filter circuitry 358 as schematically illustrated in FIG. 5 to provide such functionality. As generally depicted in FIG. 6, in such embodiments, the instrument can first be connected to a generator 300, such as one of the type disclosed above. The generator is of the type capable of commanding a programmable device to activate or deactivate generator purpose I/O lines 302. The programmable device of the connector configures the programmable device I/O lines to adapt the EGM filter circuitry 358 to the specific generator 304 (e.g., another of the generators disclosed above) identified during step 302. This results in the EGM filter circuitry 358 being optimized and adapted for the RF output by the generator 306. One example of a suitable programmable device is the Lattice LCMX02-1200HC available from Lattice Semiconductor Corp. of Hillsboro, Oregon One example of a suitable analog switch that could be used in the embodiment of FIG. 6 is a low voltage analog switch model number NLAS4599 available from ON Semiconductor of Phoenix, Arizona.

Although the present disclosure has been described with reference to preferred embodiments, workers skilled in the art will recognize that changes can be made in form and detail without departing from the spirit and scope of the present disclosure.

What is claimed is:

1. A system comprising:
an electrosurgical instrument including:
   an elongated shaft having a distal section and a proximal section;
   a handle positioned at the proximal section; and
   an electrically conductive tip at the distal section;
a connector coupled to the electrosurgical instrument, the connector configured for connecting the electrosurgical instrument to one or more devices selected from the group consisting of a radio frequency generator, a programmer/analyzer, and a pacer;
a radio frequency circuit coupled to the connector and the electrically conductive tip;
the radio frequency generator configured to provide radio frequency signals at a specific frequency that supplies ablative radio frequency energy to the electrically conductive tip; and
an electrogram filtering circuit coupled to the connector and the electrically conductive tip, the electrogram filtering circuit including:
   a first active line including a first tuned resonant filter; and
   a second return line including a second tuned resonant filter, wherein at least one of the first and the second tuned resonant filters is tuned and configured to reject signals at the specific frequency supplying ablative radio frequency energy provided by the radio frequency generator.

2. The system of claim 1, wherein the electrogram filtering circuit is positioned within the connector.

3. The system of claim 1, wherein the electrogram filtering circuit is positioned within the handle.

4. The system of claim 3, wherein the electrogram filtering circuit is rolled up and positioned within the handle.

5. The system of claim 1, wherein the electrogram filtering circuit includes a flexible substrate.

6. The system of claim 1, wherein the instrument is configured to function as a pacing device.

7. The system of claim 1, wherein the instrument is configured to function as an ablation device.

8. The system of claim 1, wherein the instrument is configured to function as a mapping device.

9. The system of claim 1, wherein the instrument is configured to function as a sensing device.

10. The system of claim, 1 wherein the instrument is configured to function as pacing device, an ablation device, a mapping device and a sensing device.

11. The system of claim, 1 wherein the instrument is configured to function as pacing device, a mapping device and a sensing device.

12. The system of claim 1, wherein each tuned resonant filter includes an inductor, capacitor and a resistor.

13. The system of claim 1, wherein each tuned resonant filter is a single stage filter.

14. The system of claim 1, wherein each tuned resonant filter is software configurable which can be tuned for a variety of rejection frequencies.

15. The system of claim 1, further comprising a programmer/analyzer.

16. The system of claim 1, further comprising a pacer.

17. The system of claim 1, wherein the connector is releasably coupled to the electrosurgical instrument.

18. The system of claim 1, and further comprising a programmable device coupled to the electrogram filtering circuit to adapt the electrogram filtering circuit to provide different rejection frequencies.

* * * * *